US006620818B1

(12) United States Patent
Davis

(10) Patent No.: US 6,620,818 B1
(45) Date of Patent: Sep. 16, 2003

(54) METHOD FOR REDUCING THE SEVERITY OF SIDE EFFECTS OF CHEMOTHERAPY AND/OR RADIATION THERAPY

(75) Inventor: Stephen Thomas Davis, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,392

(22) PCT Filed: Mar. 1, 2000

(86) PCT No.: PCT/US00/05186

§ 371 (c)(1), (2), (4) Date: Aug. 28, 2001

(87) PCT Pub. No.: WO00/78299

PCT Pub. Date: Dec. 28, 2000

(51) Int. Cl.$^7$ .................... A61K 31/517; A61K 31/519; A61K 31/44

(52) U.S. Cl. .................... 514/258; 514/291; 514/336; 514/338

(58) Field of Search .................. 514/258, 291, 514/336, 338

(56) References Cited

U.S. PATENT DOCUMENTS

| | | | | |
|---|---|---|---|---|
| 5,051,417 A | | 9/1991 | Nadler et al. | |
| 5,057,538 A | | 10/1991 | Shiraishi et al. | |
| 5,089,516 A | | 2/1992 | Shiraishi et al. | |
| 5,124,342 A | | 6/1992 | Kerdesky et al. | |
| 5,202,341 A | | 4/1993 | Shiraishi et al. | |
| 5,374,652 A | | 12/1994 | Buzzetti et al. | |
| 5,441,880 A | | 8/1995 | Beach et al. | |
| 5,443,962 A | | 8/1995 | Draetta et al. | |
| 5,449,755 A | | 9/1995 | Roberts et al. | |
| 5,488,057 A | | 1/1996 | Buzzetti et al. | |
| 5,627,207 A | | 5/1997 | Buzzetti et al. | |
| 5,672,508 A | | 9/1997 | Gyuris et al. | |
| 5,756,335 A | | 5/1998 | Beach et al. | |
| 5,770,423 A | | 6/1998 | Beach et al. | |
| 5,861,259 A | | 1/1999 | Roberts et al. | |
| 6,319,918 B1 | * | 11/2001 | Heckel et al. | 514/213.01 |
| 6,369,086 B1 | * | 4/2002 | Davis et al. | 514/338 |
| 6,387,919 B1 | * | 5/2002 | Davis et al. | 514/291 |

FOREIGN PATENT DOCUMENTS

| | | |
|---|---|---|
| EP | 0 436 333 A2 | 12/1990 |
| EP | 0 503 49 A1 | 2/1992 |
| EP | 0 503 349 B1 | 2/1992 |
| EP | 0 788 890 A1 | 2/1996 |
| WO | 93/01182 | 7/1992 |
| WO | 92/20796 A2 | 11/1992 |
| WO | 93/10242 | 11/1992 |
| WO | 94/28914 | 6/1993 |
| WO | 93/24514 | 12/1993 |
| WO | 94/23029 | 3/1994 |
| WO | 95/01349 | 5/1994 |
| WO | 96/00226 | 6/1994 |
| WO | 96/16964 | 10/1995 |
| WO | 96/22976 | 12/1995 |
| WO | 96/32380 | 3/1996 |
| WO | 96/12506 | 5/1996 |
| WO | 96/40116 | 6/1996 |
| WO | 97/25986 | 1/1997 |
| WO | 97/36867 | 2/1997 |
| WO | 97/27297 | 7/1997 |
| WO | 98/07695 | 8/1997 |
| WO | 98/07835 | 8/1997 |
| WO | 98/50356 | 11/1998 |
| WO | 99/10325 | 3/1999 |
| WO | 99/15500 | 4/1999 |
| WO | 99/52869 | 10/1999 |

OTHER PUBLICATIONS

Rozegurt, Current Opinion in Cell Biology, 1992, 4, pp. 161–165.
Wilks, Progress in Growth Factor Research, 1990, 2. pp. 97–111.
Hanks, et al., Science, 1988, 241, pp. 42–52.
Crews and Erikson, Cell, 1993, 74, pp. 215–217.
Ihle et al., Trends in Biochemical Sciences, 1994, 19, pp 222–227.
Pelech and Sanghera, Trends in Cell Biochemical Sciences, 1992, 17, pp. 233–238.
Massague and Roberts, Current Opinion in Cell Biology, 1995, 7, pp. 769–772.
Myerson et al., EMBO Journal, 1992, 11, pp. 2909–2917.
Draetta, Trends in Cell Biology, 1993, 3, pp. 287–289.
Murray and Kirschner, Nature, 1989, 339, pp. 275–280.
Solomon et al., Molecular Biology of the Cell, 1992, 3, pp. 13–27.
Ducommun et al., EMBO Journal, 1991, 10, pp. 3311–3319.
Gautier et al., Nature, 1989, 339, pp. 626–629.
Gould and Nurse, Nature, 1989, 342, pp. 39–45.
Krek and Nigg, EMBO Journal, 1991, 10, pp. 3331–3341.
Solomon et al., Cell, 1990, 63, pp. 1013–1024.
Pines, Trends in Biochemical Sciences, 1993, 18, pp. 195–197.
Sherr, Cell, 1993, 73, pp. 1059–1065.
Matsushime et al., Molecular & Cellular Biology, 1994, 14, pp. 2066–2076.

(List continued on next page.)

Primary Examiner—Zohreh Fay
Assistant Examiner—Brian S. Kwon
(74) Attorney, Agent, or Firm—John L. Lemanowicz

(57) ABSTRACT

A composition and method for preventing/reducing the severity of epithelial cytoxicity side effects such as alopecia, plantar-palmar syndrome, mucositis) induced by chemoptherapy and/or radiation therapy in a patient receiving such therapy wherein a cyclin-dependent kinase II inhibitor is contemporaneously administered to the patient.

12 Claims, No Drawings

OTHER PUBLICATIONS

Ohtsubo and Roberts, Science, 1993, 259, pp. 1908–1912.
Quelle et al., Genes & Development, 1993, 7, pp. 1559–1571.
Resnitzky et al,. Molecular & Cellular Biology, 1994, 14, pp. 1669–1679.
Girard et al., Cell, 1991, 67, pp. 1169–1179.
Pagano et al., EMBO Journal, 1992, 11, pp. 961–971.
Rosenblatt et al., Proceedings of the National Academy of Science USA, 1992, 89, pp. 2824–2828.
Walker and Maller, Nature, 1991, 354, pp. 314–317.
Zindy et al., Biochemical & Biophysical Research Communications, 1992, 182, pp. 1144–1154.
Pines, Current Opinion in Cell Biology, 1992, 4, pp. 144–148.
Lees, Current Opinion in Cell Biology, 1995, 7, pp. 773–780.
Hunter and Pines, Cell, 1994, 79, pp. 573–582.
Brickell, Critical Reviews in Oncogenesis, 1992, 3, pp. 401–446.
Courtneidge, Seminars in Cancer Biology, 1994, 5, pp. 239–246.
Powis, Pharmacology & Therapeutics, 1994, 62, pp. 57–95.
Buchdunger et al., Proc. Nat. Acad. Sci. USA, vol. 92, 1995, pp. 2258–2262.
Hosoi et al., Journal of Biochemistry (Tokyo), 1995, 117, pp. 741–749.
Aplin et al., Journal of Neurochemistry, 1996, 67, pp. 699–707.
Tanaka et al., Nature, 1996, 383, pp. 528–531.
Borthwick et al., Biochemical & Biophysical Research Communications, 1995, 210, pp. 738–745.
Badger et al., Journal of Pharmacology & Experimental Therapeutics, 1996, 279, pp. 1453–1461.
Shawyer et al., Drug Discovery Today, 1997, 2, pp. 50–63.
He et al., Journal of Virology, 1997, 71, pp. 405–411.
Myers et al., Bioorganic & Medicinal Chemistry Letters, 1997, 7, pp. 421–424.
Vousden, FASEB Journal, 1993, 7, pp. 872–879.
Stone et al., Cancer Research, 1996, 56, pp. 440–452.
Perkins et al., Science, 1997, 275, pp. 523–527.
Baeuerle and Henkel, Annual Review of Immunology, 1994, 12, pp. 141–179.
Beg and Baltimore, Science, 1996, 274, pp. 782–784.
Wang et al., Science, 1996, 274, pp. 784–787.
Van Antwerp et al., Science, 1996, 274, pp. 787–789.
Armstrong, Clinical Infectious Diseases, 1993, 16, pp. 1–7.
Osmani et al., EMBO Journal, 1991, 10, pp. 2669–2679.
Kohn et al., Journal of Cellular Biochemistry, 54, 1994, pp. 440–452.
Osmani et al., Cell, vol. 67, Oct. 18, 1991, pp. 283–291.
Mohammed Kamel et al., "Monoazo Metal Complex Forming Dyes Part v Dyes Derived form Isatin," J. Chem. U.A.R. 9, No. 2, 139–144 (1996).
Vishnu J. Ram, et al., "Pesticidal mannich Bases Derived from Isatinimines," J Heterocycle Chem. pp. 1367–1369, vol. 23, Sep.–Oct. 1986.
Xiaoyun Wu et al., "Chemical Constiuents of Isatis Indigotica," Planta Medica, pp. 55–57, 1997.
Cline, B.W., "Prevention of Chemotherapy–Induced Alopecia: A Review of the Literature," Cancer/Nursing, Jun. 1984, pp. 221–227.
Gray, N.S. et al., "Exploiting Chemical Libraries, Structure, and Genomics in the Search for Kinase Inhibitors," Sicence, vol. 281, Jul. 24, 1998, pp. 533–538.
Hussein, A.M., "Chemotherapy–Induced Alopecia: New Developments," Southern Medical Journal, May 1993, vol. 86, No. 5, pp. 489–496.
Hussein, A.M., "Protection from Chemotherapy–Induced Alopecia in a Rat Model," Science, vol. 249, Sep. 28, 1990, pp. 1564–1566.
Lauer, A.C. et al., "Transfollicular Drug Delivery," Pharmaceutical Research, vol. 12, No. 2, 1995, pp. 179–186.
Li, L., et al., "The Feasibility of Targeted Selective Gene Therapy of the Hair Follicle," Nature Medicine, vol. 1, No. 7, Jul. 1995, pp. 705–706.
Pallumbo, Giuseppe A., et al., "The Tyrphostin AG17 Induces Apoptosis and Inhibition of cdk2 Activity in a Lymphoma Cell Line that Overexpresses bcl–2," Cancer Research, 57, Jun. 15, 1997, pp. 2434–2439.
Sedlacek, Hans H., et al., "Flavopiridol (L86 82875; NSC 649890), a New Kinase Inhibitor for Tumor Therapy," International Journal of Oncology, vol. 9, 1996, pp. 1143–1168.
Toledo, Leticia M. et al., "Structures of Staurosporine Bound on CDK2 and cAPK–New Tools for Structure–based Designed of Protein Kinase Inhibitors," Structure, 1997, vol. 5, No. 12, pp. 1551–1556.

* cited by examiner

METHOD FOR REDUCING THE SEVERITY OF SIDE EFFECTS OF CHEMOTHERAPY AND/OR RADIATION THERAPY

This application is filed pursuant to 35 U.S.C. §371 as a United States National Phase Application of International Application No. PCT/US00/05186 filed Mar. 1, 2000, which claims priority from 9904932.2 filed Mar. 4,1999.

The present invention relates generally to cyclin-dependent kinase II inhibitor compounds having utility as pharmacological agents for preventing/reducing the severity of epithelial cytotoxicity side effects of chemotherapy and/or radiation therapy, including alopecia plantar-palmar syndrome and/or mucositis. The invention also relates to a corresponding method of preventing/reducing the severity of such side effects, by administration of such a pharmalogical agent to a patient subjected to chemotherapy and/or radiation therapy treatment.

BACKGROUND OF THE INVENTION

Protein kinases play a critical role in the control of cell growth and differentiation and are key mediators of cellular signals leading to the production of growth factors and cytokines. See, for example, Schiessinger and Ulirich, *Neuron* 1992, 9, 383. A partial non-limiting list of such kinases includes abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, IGF-1R, IKK, IKK1, IKK2, JKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKCα, PKCβ, PKCδ, PKCε, PKCγ, PKCλ, PKCμ, PKCζ, PLK1, Polo-like kinase, PYK2, tie1, tie2, TrkA, TrkB, TrkC, UL13, UL97, VEGF-R1, VEGF-R2, Yes and Zap70. Protein kineses have been implicated as targets in central nervous system disorders such as Alzheimer's (Mandelkow, E. M. et al. *FEBS Lett.* 1992, 314, 315. Sengupta, A. et al. *Mol. Cell. Biochem.* 1997, 167,99), pain sensation (Yashpal, K. *J. Neurosci.* 1995, 15, 3263–72), inflammatory disorders such as arthritis (Badger, *J. Pharm. Exp. Ther.* 1996, 279, 1453), psoriasis (Dvir, et al. *J. Cell Biol.* 1991, 113, 857), and chronic obstructive pulmononary disease, bone diseases such as osteoporosis (Tanaka et al, *Nature*, 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat. Acad. Sci USA* 1991, 92, 2258), autoimmune diseases and transplant rejection (Bolen and Brugge, *Ann. Rev. Immunol.* 1997, 15, 371) and infectious diseases such as viral (Littler, E. *Nature* 1992, 358, 160), and fungal infections (Lum, R. T. PCT Int. Appl., WO 9805335 A1 980212).

Chemotherapeutic techniques and radiation therapy techniques are well-established in the treatment of neoplastic conditions of various types. As concomitant side-effects to the administration of chemotherapy and/or radiation therapy, patients commonly experience severe host epithelial cell toxicity. The consequences of damage to the proliferating epithelium induced by chemotherapy frequently include hair loss (alopecia), plantar-palmar syndrome and mucositis; such side effects, especially mucositis, are also known to occur as a result of radiation therapy. These side-effects may be of varying severity, depending on the type, dosages and dosing schedule of the respective chemotherapy and/or radiation therapy involved.

SUMMARY OF THE INVENTION

The present invention provides a novel approach to preventing/reducing the severity of epithelial cytotoxicity side effects such as alopecia, plantar-palmar syndrome and/or mucositis in a subject receiving chermotherapy and/or radiation therapy, by administering to such subject an effective amount of a cyclin-dependent kinase II inhibitor.

A wide variety of particular cyclin-dependent kinase II inhibitor species useful in the broad practice of the present invention are hereinafter more fully described.

The cyclin-dependent kinase inhibitor is preferably non-systemically administered to the subject, more preferably topically.

The cyclin-dependent kinase II inhibitor may be administered topically to prevent/reduce the severity of alopecia incident to chemotherapy and/or radiation therapy, by application of the inhibitor compound, or a formulation containing same, to a corporeal locus susceptible to alopecia. For example, a topical formulation may be made up with the cyclin-dependent kinase II inhibitor present in an effective amount and such topical formulation may then be administered to the subject's scalp and/or facial areas, to combat alopecia incident to chemotherapy and/or radiation therapy treatment.

For preventing/reducing the severity of plantar-palmar syndrome incident to chemotherapy and/or radiation therapy, the cyclin-dependent kinase II inhibitor may be topically administered to the plantar and/or palmar regions that are susceptible to lesioning as a concomitant condition of such therapeutic treatment.

In preventing/reducing the severity of mucositis as a, side effect incident to chemotherapeutic and/or radiation therapy treatment, the cyclin-dependent kinase II inhibitor is preferably administered topically to mouth and throat mucosa of the oral cavity.

In a combination therapeutic approach according to one embodiment of the invention, the patient receiving chemotherapy and/or radiation therapy may be contemporaneously administered the cyclin-dependent kinase II inhibitor in accordance with a selected dosage regimen that is effective to prevent/reduce the severity of two or more of the aforementioned side effects. Such administration is desirably of a non-systemic character, being topically applied to head regions susceptible to occurrence or progression of alopecia, being topically applied to plantar and/or palmar regions susceptible to the occurance or progression of plantar-palmar lesions, and/or being topically administered to oral cavity mucosa in the mouth and throat areas susceptible to occurrence or progression of mucositis.

The invention in another aspect relates to a cytoprotective composition for preventing/reducing the severity of epithelial cytotoxicity side effects incident to the administration of chemotherapy and/or radiation therapy, e.g., alopecia, plantar-palmar syndrome and/or mucositis. Such composition is suitably formulated to comprise an effective amount of a cyclin-dependent kinase II inhibitor for the prevention or reduction in the severity of the epithelial cytotoxicity side effects of the chemotherapy and/or radiation therapy. The composition may be formulated for such purpose with one or more pharmaceutically acceptable carriers, excipients or diluents.

Other aspects and features of the invention will be more fully apparent from the ensuing disclosure and appended claims.

DETAILED DESCRIPTION OF THE INVENTION, AND PREFERRED EMBODIMENTS THEREOF

The present invention provides a method and composition for preventing/reducing the severity of epithelial cytotoxicity side effects, e.g., alopecia, plantar-palmar syndrome and/or mucositis, in a subject receiving chemotherapy and/or radiation therapy, involving administration to the subject of an effective amount of a cyclin-dependent kinase II inhibitor.

Cyclin-dependent kinase II (sometimes hereinafter referred to as "CDK2") is a protein serine/threonine kinase that is required for progression of cells through the G1 and S phases of the cell cycle. Inhibition of CDK2 in normal cells results in a reversible cell cycle arrest and can therefore protect cells from antineoplastic agents with cytotoxic activity dependent on progression through the cell cycle. The present invention exploits this characteristic.

In one preferred aspect of the present invention, an inhibitor of CDK2 is topically applied to the scalp ad optionally other hirsute areas to prevent alopecia, one of the most common and distressing side effects of chemotherapy and/or radiation therapy. By direct delivery of the CDK2 inhibitor agent to the follicular target, systemic exposure of the compound is minimized, without compromising the antineoplastic efficacy of the chemotherapeutic agent.

In other aspects of the e invention, the CDK2 inhibitor is topically applied to the hands and/or feet of a patient, to prevent or reduce the severity of plantar-palmar syndrome, and/or is topically applied to the mouth and throat mucosa of the oral cavity to prevent or reduce the severity of mucositis incident to chemotherapy and/or radiation therapy treatment.

The cyclin-dependent kinase II inhibitor of the invention may comprise any suitable compound having inhibitory action on cyclin-dependent kinase II activity, i.e. a compound that is effective to suppress or ameliorate cyclin-dependent kinase II activity so as to prevent/reduce the severity of epithelial cytotoxicity side effects such as alopecia, plantar-palmar syndrome and/or mucositis incident to the administration of chemotherapy and/or radiation therapy.

Illustrative cyclin-dependent kinase II inhibitors that may be employed in the broad practice of the invention to prevent/reduce the severity of epithelial cytotoxicity side effects of chemotherapy and/or radiation therapy, such as alopecia, plantar-palmar syndrome and/or mucositis, include the cyclin-dependent kinase II inhibitor compounds described in the following references, as well as in the references identified in the Bibliography set forth hereinafter, the disclosures of all of which are hereby incorporated herein by reference in their respective entireties:

(A) substituted oxindole derivatives described in International Patent Application No. PCT/EP98/05559 filed Sep. 3, 1998 for "Substituted Oxindole Derivatives,"
(B) purine derivatives described in International Publication WO97/20842 of CNRS Center Natural Research;
(C) pyridylpyrimidinamine derivatives described in International Publication WO95/09852 of Ciba-Geigy (Novartis);
(D) 2,6,9-trisubstituted compounds described in International Publication WO98/05335 of CV Therapeutics;
(E) 4H-1-benzopyran-4-one derivatives described in German Patent 3836676 of Hoechst AG;
(F) 2-thiol and 2-oxo-flavopiridol analogues described in U.S. Pat. No. 5,705,350, and in U.S. Pat. No. 5,849,733;
(G) pyrido [2,3-D] pyrimidines and 4-aminopyrimidines described in International Publication WO98/33798 of Wamer Lambert Company as well as in U.S. Pat. Nos. 5,776,942; 5,733,913; 5,223,503; 4,628,089; 4,536,575; 4,431,805; and 4,252,946;
(H) antiviral CDK2 inhibitor compounds described in International Publication WO98/39007 of the. University of Texas;
(I) chimeric CDK2 inhibitors described in International Publication WO97/27297 of Mitotix Inc.:
(J) the 2,6,9-trisubstituted purines described in Imbach, P., et al., 2,6,9-Trisubstituted Purines: Optimization Towards Highly Potent and Selective CDK1 Inhibitors, Bioorganic and Medicinal Chemistry Letters, 9 (1999), 91–96.
(K) the peptide inhibitors described in U.S. Pat. No. 5,625, 031 issued Apr. 29, 1997 to K. R. Webster, et al.
(L) CDK2 inhibitor antisense sequences described in U.S. Pat. No. 5,821,234 issued Oct. 13, 1998 to Viktor J. Dzau;
(M) the C2 alkynylated purines described in Legraverend, M., et al., Synthesis of C2 Alkynylated Purines, a New Family of Potent Inhibitors of Cyclin-Dependent Kinases, Bioorganic & Medicinal Chemistry Letters 8 (1998) 793–798; and
(N) the tyrphostins described in Kleinberger-Doron, N., et al., Inhibition of Cdk2 Activation by Selected Tyrphostins Causes Cell Cycle Arrest at Late G1 and S Phase, Experimental Cell Research 241, 340–351 (1998).

In addition to the use of specific compounds shown to be CDK2 inhibitors, the present invention also extends to the use of pharmaceutically acceptable salts, solvates, biohydrolyzable carbonates, biohydrolyzable ureides, biohydrolyzable esters, biohydrolyzable amides, biohydrolyzable carbamates, affinity reagents or prodrugs thereof in either crystalline or amorphous form.

The therapeutic compositions of the present invention may include one or more than one cyclin-dependent kinase II inhibitor agent, as suitable to achieve the desired efficacy in a given end use application of the invention.

One class of compounds that may be usefully employed in the practice of the invention is described in International Patent Application PCT/EP98/05559, the entire disclosure of which is incorporated herein by reference. Such class comprises compounds of the Formula (A):

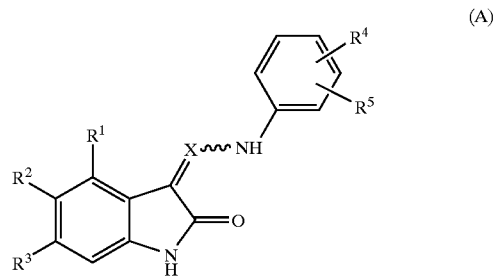

(A)

wherein:
X is N, CH, CCF₃, or C(C$_{1-12}$ aliphatic);
R¹ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R⁶-Aryl-C$_{1-12}$ aliphatic, Cyc, CyC-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen (e.g., fluoro, bromo, iodo), cyano, sulfonamide, or nitro, where $R^6$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, and $C_{1-12}$ aliphatic-aminosuifonyl, where Aryl and Het are as defined below;

further wherein $R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, carbo-$C_{1-12}$ alkoxy, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$ is selected from the group consisting of: suifonic acid, $C_{1-12}$ aliphatic-sulfonyl, sulfonyl-$C_{1-12}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-sulfonyiamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Arylaminosulfonyl, $(R^8)_{1-3}$-Arylsulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring being selected from the group as defined for Het below, or any of said fused rings optionally substituted by $C_{1-12}$aliphatic, oxo or dioxo;

$R^6$ is selected from the group consisting of $C_{1-12}$aliphatic, hydroxy, $C_{1-12}$alkoxy, or halogen;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$ aliphatic, Het-$C_{1-12}$ alkoxy, di-Het-$C_{1-12}$ alkoxy Aryl, Aryl-$C_{1-12}$ aliphatic, Aryl-$C_{1-12}$ alkoxy, Aryl-carbonyl, $C_{1-18}$ alkoxyalkoxyalkoxyalkoxyaliphatic, or hydroxyl where Het and Aryl are as defined below;

$R^8$ is selected from the group consisting of: hydrogen, nitro, cyano, $C_{1-12}$ alkoxy, halo, carbo-$C_{1-12}$ alkoxy and halo-$C_{1-12}$ aliphatic;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiadzole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are, biohydrolyzable.

Illustrative species of cyclin-dependent kinase II inhibitors that may be usefully employed in the practice of the present invention include the following compounds within the foregoing formula (A) (of formulae (A1), (A2), and (A3) respectively):

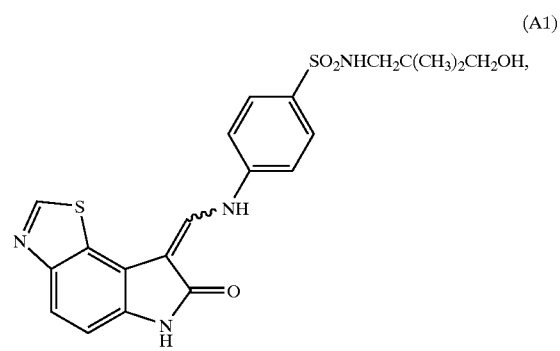

(A1)

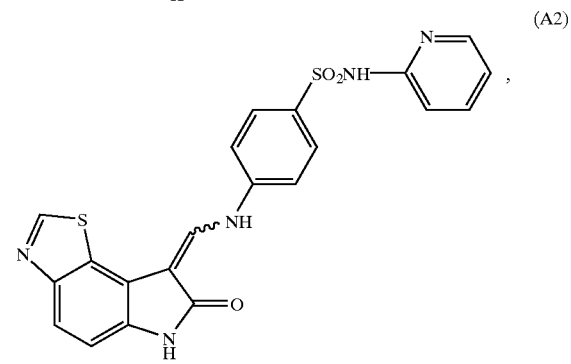

(A2)

-continued

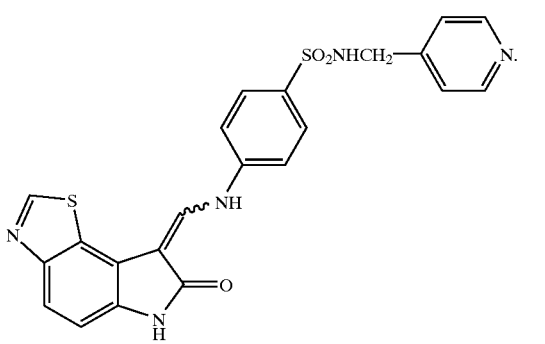

(A3)

The CDK2 inhibitor compound that is selected for use in a given application of the methodology of the present invention may then be formulated as the active ingredient in a pharmaceutically acceptable composition, for topical or otherwise non-systemic administration to a subject (e.g., a mammalian subject such as a human subject), to prevent/reduce the severity of epithelial cytotoxicity side effects (e.g., alopecia, plantar-palmar syndrome, and/or mucocitis) induced by chemotherapy and/or radiation therapy contemporaneously being administered to the subject.

To prevent/reduce the severity of alopecia induced by chemotherapy and/or radiation therapy in a subject receiving such therapy, the CDK2 inhibitor compound is preferably administered topically to the corporeal locus that is susceptible to alopecia, such as the head (e.g., the scalp, eyebrow regions, beard and mustache areas, etc.).

For such topical application, the cyclin dependant kinase II inhibitor compound may be formulated in a topical administration formulation, by combination of the compound with a selected pharmaceutically acceptable vehicle (carrier, diluent or excipient), so that the amount of the compound in the formulation is sufficient to achieve the prevention or reduction in severity of the alopecia side effect, when administered in accordance with an appropriately designed treatment protocol. The formulation can be in any useful dosage unit form for corresponding administration.

Formulations of the thiazole-oxindole compound may be constituted and administered in any suitable manner, such as in a liquid formulation for aerosolized spray administration to the head region of a subject susceptible to chemotherapy-induced alopecia, or by a dermal patch or dressing containing the CDK2 inhibitor formulation in a releasable form, for positioning on the head in contact with the area of susceptibility.

The formulation may alternatively be prepared as a lotion, salve, gel, foam, paste, oil, creme, or other suitable form, for administration to the appropriate corporeal locus, e.g., to the scalp or other area of the head for preventing/reducing the severity of alopecia, with initial administration being followed by massage, brushing, or toweling to distribute the formulation on the scalp evenly for uniformity of therapeutic effect.

As one example of compositions that may be used for topical adminstration of the CDK2 inhibitor agents of the invention to the corporeal locus of a subject receiving chemotherapy and/or radiation therapy, a formulation of the type described in Tata, S., et al., Relative Influence of Ethanol and Propylene Glycol Cosolvents on Deposition of Minoxidil into the Skin, Journal of Pharmaceutical Sciences, Vol. 83, No. 10, October 1994, pp. 1508–1510, may be employed. Such a formulation may comprise a 2% solution of the active ingredient in 60% ethanol, 20% propylene glycol and 20% water, for topical administration of the solution to the scalp.

Still other formulations that may be usefully employed for topical administration of the CDK2 inhibitor agents of the invention, include the formulations identified in U.S. Pat. Nos. 5,849,733; 5,807,698; 5,625,031; and 5,486,509, the disclosures of which are incorporated herein by reference in their entireties.

Additional illustrative examples of formulations that may be usefully employed for the topical administration of the CDK2 inhibitor agent of the invention include: the lipid based formulations described in Hoffman, R. M., et al., Liposomes Can Specifically Target Entrapped Melanin To Hair Follicles in Histocultured Skin, In Vivo Cell. Dev. Biol., Vol. 29A: 192–194, March 1993, and in Niemiec, S. M., et al., Influence of Nonionic Liposomal Composition on Topical Delivery of Peptide Drugs into Pilosebaceous Units: An in Vivo Study Using the Hamster Ear Model, Pharmaceutical Research, Vol. 12, No. 8, 1995, pp. 1184–1188; and the polymeric microsphere formulations described in Rolland, A., et al., Site-Specific Drug Delivery to Pilosebaceous Structures Using Polymeric. Microspheres, Pharmaceutical Research, Vol. 10, No. 12, 1993, pp. 1738–1744.

The formulation may be constituted to provide an appropriate dose for a desired dosing schedule. The dosage and dosage schedule may be readily determined for a given subject, within the skill of the art, based on the character of the chemotherapy and/or radiation therapy being employed.

Analogous considerations apply to the formulation and administration of the CDK2 inhibitor for preventing/reducing the severity of plantar-palmar syndrome, involving topical administration to the areas of the hands and feet susceptible to the syndrome as a side-effect of chemotherapy and/or radiation therapy.

For preventing/reducing the severity of mucositis, the cyclin-dependent kinase II inhibitor may be formulated in a suitable topical formulation for application to the oral cavity mucosa. Illustrative delivery systems for the cyclin-dependent kinase II inhibitor of the invention, as used to combat mucositis, include the formulations and delivery techniques described in Cullinan U.S. Pat. No. 5,496,828 issued Mar. 5, 1996 for "Methods of Inhibiting Ulcerative Mucositis." Useful formulations may include the active ingredient and excipients, diluents, or carriers, formed into tablets, capsules, sprays, mouthwashes, lozenges, troches, pastilles, lollipops, suspensions, powders and the like, for application to the mucosa of the oral cavity.

Acceptable daily dosages of the CDK2 inhibitor for preventing/reducing the severity of epithtelial cytotoxicity side effects induced by chemotherapy and/or radiation therapy, may be from about 0.1 to about 1000 mg/day, and preferably from about 0.2 to about 100 mg/day.

The cyclin-dependent kinase II inhibitor in the preferred practice of the invention is administered contemporaneously with the chemotherapy and/or radiation therapy treatment (i.e., simultaneously with, or sufficiently near in time to, the chemotherapy and/or radiation therapy, so as to achieve a preventative or ameliorative effect on the epithelial cytotoxicity side effect that would otherwise be presented in the absence of the CDK2 inhibitor). The chemotherapy and/or radiation therapy may be of any appropriate type for the neoplastic condition, or other disease state or condition, of the patient being treated. As an illustrative example, the chemotherapy may comprise administration of chemotherapeutic agents, including cycle-specific agents (such as cytosine arabinoside (ARA-C)) and non-cycle-specific agents (such as Cytoxan), individually or in combination with one another.

The cyclin-dependent kinase II inhibitor in one embodiment of the invention is administered 1–4 times in a chemotherapeutic cycle, as a cytoprotective composition for preventing/reducing the severity of epithelial cytotoxicity side effects such as alopecia, plantar-palmar syndrome and/or mucositis, in a subject receiving chemotherapy and/or radiation therapy.

In the specific application of preventing/reducing the severity of chemotherapy-induced alopecia, the cyclin-dependent kinase II inhibitor effects a desired temporary arrest of the hair follicle cell cycle by inhibition of cyclin-dependent kinase II activity. For such purpose, the inhibitor agent, formulated in a suitable topically administerable formulation, may be applied 1–2 times per chemotherapeutic cycle prior to and during the time of administration of chemotherapy, in one specific preferred illustrative embodiment.

In one preferred aspect of the invention, cyclin-dependent kinase II inhibitor agents that are topically administerable to prevent/reduce the severity of chemotherapy-induced alopecia, are assessed for efficacy and selected for use based on one or more of the following characteristics:

(1) an IC50 value of less than 2.5 nanoMolar and preferably less than 20 nanoMolar against CDK2;
(2) an IC50 value of less than 1.5 microMolar and preferably less than 5 microModlar in a G1 checkpoint assay;
(3) exhibition of reproducible protection in a baby rat alopecia model using at least 2 different cytotoxic regimens one of which includes an alkylating agent (e.g., a regimen involving doxorubicin/cyclophosphamide (anthracyclin/alkylating agent), etoposide (topoisomerase II inhibitor), taxol, etc.);
(4) a topical dose of 10 mg/kg of body weight of the subject yielding a plasma concentration of less than 15 nanoMolar, and preferably a systemic exposure to less than 0.01 of the IC50 concentration for protection of the HT29 tumour cell line;
(5) an acceptable dermal irritation profile; and
(6) suitability for the particular topical formulation to be employed (in terms of compatibility, bioavailability, etc.).

The compound of the invention may be formulated for topical administration in any suitable manner to prevent/reduce the severity of plantar/palmar syndrome, involving a suitable dosing and treatment regimen for the patient receiving chemotherapy and/or radiation therapy.

For the prevention/reduction of severity of mucositis in a patient receiving chemotherapy and/or radiation therapy, the compound of the.invention in an appropriate form is most preferably formulated for topical administration to the oral cavity mucosa, in a mouthwash, lozenge or lollipop.

The invention may be practiced with a wide variety of CDK2 inhibitor compounds, some of which are described more fully below.

One class of compounds that may be usefully employed in the practice of the invention includes C2 alkynylated purines, including CDK2 inhibitor compounds of formula (B) below:

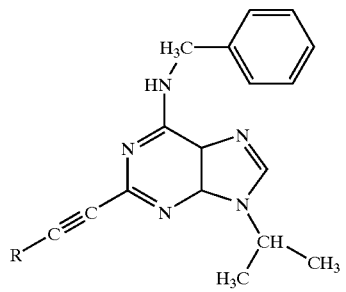

and their further saturated derivatives, wherein R may comprise a substituent such as:

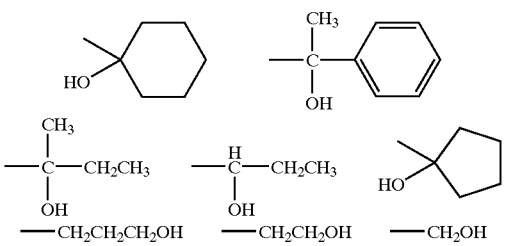

as more fully described in Legraverend, M., et al., Synthesis of C2 Alkynylated Purines, a New Family of Potent Inhibitors of Cyclin-Dependent Kinases, Bioorganic & Medicinal Chemistry Letters 8 (1998) 793–798.

Other purine compounds that may be usefully employed in the broad practice of the invention include those disclosed in International Publication WO 97/20842 published Jun. 12, 1997 and entitled, "NOVEL PURINE DERIVATIVES HAVING, IN PARTICULAR, ANTIPROLIFERATIVE PROPERTIES, AND BIOLOGICAL USES THEREOF" (CENTRE NATIONAL DE LA RECHERCHE SCIENTIFIQUE (C.N.R.S.), which describes 2-, 6- and 9-substituted purine derivatives, such as 2-(1-R hydroxymethylpropylamino)-6-benzylamino-9-isopropyl-purine, having antiproliferative properties, and including roscovitine and olomoucine, whose formulae are set out below:

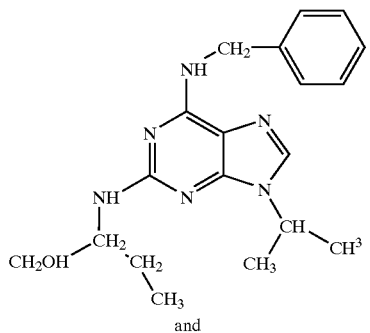

and

-continued

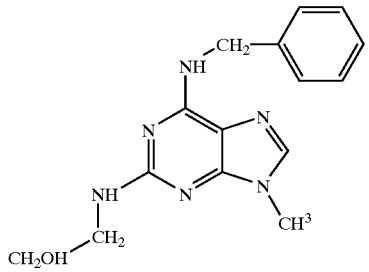

Another class of CDK2 inhibitor compounds that may be usefully employed in the practice of the invention includes 2-thio or 2-oxo flavopiridol analogs, as for example the compounds of the formula:

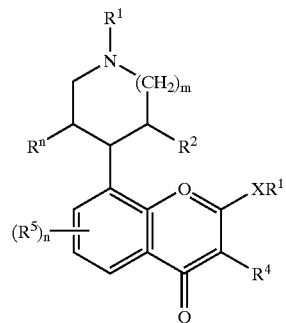

wherein:

X is oxygen or sulfur;

$R^1$ is hydrogen, alkyl, aryl, arylalkyl, cycloalkyl, —$(CH_2)_q$—$NR^7R^8$, alkylcarbonyl, arylcarbonyl, arylalkylcarbonyl, alkoxycarbonyl, arylalkyloxycarbonyl or aryloxycarbonyl;

$R^2$ is hydrogen, alkyl, aryl, arylalkyl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio, or arylthio;

$R^3$ is alkyl, cycloalkyl, aryl, arylalkyl, heterocycle, or heterocycloalkyl;

$R^4$ is hydrogen, alkyl, aryl, arylalkyl, nitro, amino, —$(CH_2)_p$—$NR^7R^8$, halogen, hydroxy, alkoxy, carboxy, heterocycle or alkyloxycarbonyl;

$R^5$ is hydrogen, alkyl, arylalkyl, aryl, cycloalkyl, hydroxy, alkoxy, arylalkoxy, aryloxy, alkylcarbonyloxy, !arylalkylcarbonyloxy, arylcarbonyloxy, carboxy, alkyloxycarbonyl, arylalkoxycarbonyl, cyano, nitro, —$NR^7R^8$, halogen, alkylhalo, —CHO, alkylS(O)$_m$— or —OC(O)$NR^7R^8$;

$R^6$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, amino, cyano, nitro, —$NR^7R^8$, halogen, alkylhalo, —CHO, alkylS(O)$_m$— or —OC(O)$NR^7R^8$, $NR^7R^8$, thiol, alkylthio, arylalkylthio or arylthio;

$R^7$ and $R^8$ are independently hydrogen, alkyl, aryl, arylalkyl, cycloalkyl, heterocycle or alkylcarbonyl; or $R^7$ and $R^8$ together with a nitrogen atom to which they are bonded can form a heterocycle;

m is an integer of 0 to 2;

n is an integer of 0 to 3;

p is an integer of 1 to 3; and q is an integer of 2 to 5.

Such flavopiridol derivatives are more fully described in U.S. Pat. No. 5,849,733 and in International Publication WO 97/42949 published Nov. 20, 1997, "2-THIO OR 2-OXO FLAVOPIRIDOL ANALOGS" (BRISTOL-MYERS SQUIBB COMPANY).

Another illustrative class of CDK2 inhibitor compounds usefully employed in the practice of the invention includes the compounds of the formula:

Formula C

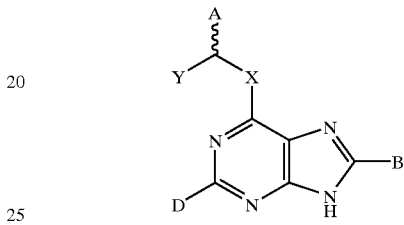

wherein

X is O, S or $CHR_x$ where $R_x$ is H or $C_{1-4}$ alkyl; D is H, halo or $NZ_1 Z_2$ where $Z_1$ and $Z_2$ are each independently H or $C_{1-4}$ alkyl or $C_{1-4}$ hydroxyalkyl; A is selected from H, $C_{1-4}$ alkyl, $C_{1-4}$ alkoxy; hydroxy, $CH_2 (CH_2)$ n OH (n=1–4), and $NR_{a1}R_{a2}$ where $R_{a1}$, and $R_{a2}$ are each independently H or $C_{1-4}$ alkyl; B is selected from H, $C_{1-4}$ alkyl, $C_{1-4}$ alkoxy, $CF_3$, an optionally substituted aryl (e.g. phenyl) or an optionally substituted aralkyl (e.g. benzyl), and an hydroxy group that provides a C=O tautomer; and Y is or includes an optionally substituted 4- to 8-membered carbocyclic or heterocycle ring; or comprises an optionally substituted linear or branched hydrocarbon chain.

Such purine derivatives are more fully described in International Publication WO 99/02162 published Jan. 21, 1999 entitled, "CYCLIN DEPENDENT KINASE INHIBITING PURINE DERIVATIVES" (NEWCASTLE UNIVERSITY VENTURES LIMITED).

A further class of CDK2 inhibitor compounds useful in preventing epithelial cytotoxicity incident to chemotherapy and/or radiation therapy in accordance with the present invention include the compounds described in International Publication WO 98/33798 published Aug. 6, 1998 and entitled, "PYRIDO[2,3-D] PYRIMIDINES AND 4-AMINOPYRIMIDINES AS INHIBITORS OF CELLULAR PROLIFERATION" (WARNER LAMBERT COMPANY), which discloses 7,8-dihydro-2-(amino and thio)pyrido[2,3-d]pyrimidines and 2,4-diaminopyrimidines that are potent inhibitors of cyclin-dependent kinases (cdks) and growth factor-mediated kinases, and are described as being useful for treating cell proliferatives disorders, such as cancer and restenosis. Such compounds are of Formula D1 and Formula D2 below:

Formula D1

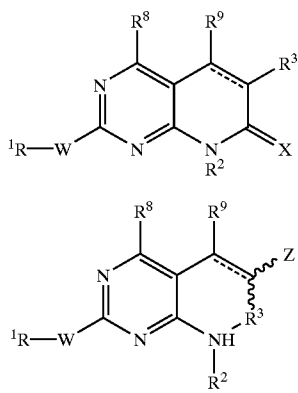

Formula D2 wherein W is NH, S, SO, or $SO_2$, $R_1$ includes phenyl and substituted phenyl, $R_2$ includes alkyl and cycloalkyl, $R_3$ includes alkyl and hydrogen, $R_8$ and $R_9$ include hydrogen and alkyl, and Z is carboxy.

Another category of compounds that may be usefully employed in the practice of the invention includes the 4H-1-benzopyran-4-one derivatives described in German Patent DE 3836676 (Hoechst AG).

A further class of CDK2 inhibitors includes tyrphostins, such as for example tyrphostins from the AG555/AG494 family as described in N. Kleinberger-Doron, et al., Inhibition of Cdk2 Activation by Selected Tyrphostins Causes Cell Cycle Arrest at Late G1 and S Phases, Experimental Cell Research 241, 340–351 (1998).

Still other CDK2 inhibitors that may be usefully employed in the practice of the invention include the 2, 6, 9-trisubstituted purine compounds described in International Publication WO 98/05335 published Feb. 12, 1998, "PURINE INHIBITORS OF CYCLIN DEPENDENT KINASE 2 AND I" (CV THERAPEUTICS, INC.) of the formulae:

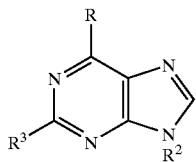

wherein R is, halogen, $XR_1$; X=NH, O, $SO_2$; $R_1$=alkyl, cycloalkyl, heterocycle, aryl, heteroalkyl; $R_2$=H, alkyl, cycloalkyl, aryl, heteroalkyl; $R_3$=halogen, OH, SH, alkoxy, alkylthio, amino, N-bonded heterocycle.

Another aspect of the present invention relates to the use of a CDK2 inhibitor species, in coadministration or alternating administration with previously known anti-alopecia and/or anti-mucositis therapies for more effective treatment of the patient undergoing chemotherapy.

By way of specific example, the CDK2 inhibitor agent may be administered to a patient undergoing chemotherapy, concurrently with administration to the patient of an anti-mucositis agent, such as the mucositis-preventing/reducing the severity of compounds of the formula:

wherein $R^1$ and $R^3$ are independently hydrogen, —$CH_3$, —C(O)—($C_{1-6}$ alkyl), or —C(O)—Ar, wherein Ar is optionally substituted phenyl;

$R^2$ is selected from the group consisting of pyrrolidine, hexamethyleneamino, and piperidino; and pharmaceutically acceptable salts and solvates thereof, as more fully described in U.S. Pat. No. 5,496,828.

Various other co-administered active agents may be employed in combination with the CDK2 inhibitor agent(s) in a course or regimen of therapy, for enhanced therapeutic effect.

As used herein, the term "solvate" is a complex of variable stoichiometry formed by a solute and a solvent. Such solvents for the purpose of the invention may not interfere with the biological activity of the solute. Solvents may be, by way of example, water, ethanol, or acetic acid.

As used herein, the terms "biohydrolyzable carbonate", "biohydrolyzable ureide" and "biohydrolyzable carbamate" include carbonates, ureides, and carbamates, respectively, of a CDK2 inhibitor compound, which carbonates, ureides, and carbamates, do not completely diminish the biological activity of the parent substance. Such carbonates, ureides, and carbamates may confer on the parent compound advantageous properties in vivo, such as improved duration of action, onset of action, and the like. Also included are compounds which are relatively biologically inactive but which are converted in vivo by the subject to the biologically active principle. An advantage of such biohydrolyzable forms is that, for example, they facilitate improved oral administration because the carbonates, ureides, and carbamates are more readily absorbed from the gut and are then transformed to an active compound in plasma. Many examples of such biohydrolyzable compounds are known in the art and include, by way of example, lower alkyl carbamates.

As used herein, the term "biohydrolyzable ester" is an ester of an active compound which does not completely diminish the biological activity of the parent substance. Such esters may confer on the parent compound advantageous properties in vivo, such as improved duration of action, onset of action, and the like. Also included are esters which are relatively biologically inactive but which are converted in vivo by the subject to the biologically active principle. An advantage of such biohydrolyzable forms is that, for example, they facilitate improved oral administration because they are more readily absorbed from the gut and are then transformed to an active compound in plasma. Many examples of such biohydrolyzable esters are known in the art and include, by way of example, lower alkyl esters, lower acyloxy-alkyl esters, lower alkoxyacyloxyalkyl esters, alkoxyacyloxy esters, alkyl acylamino alkyl esters and choline esters.

As used herein, the term "biohydrolyzable amide" is an amide of an active parent compound which does not completely diminish the biological activity of the parent compound. Such amides may confer on the parent compound advantageous properties in vivo, such as improved duration of action, onset of action, and the like. Also included are amides which are relatively biologically inactive but which are converted in vivo by the subject to the biologically active principle. An advantage of such biohydrolyzable forms is that, for example, they facilitate improved oral administration because they are more readily absorbed from the gut and are then transformed to an active compound in plasma. Many examples of such biohydrolyzable are known in the art and include, by way of example, lower alkyl amides, α-amino acid amides, alkoxyacyl amides and alkylaminoalkylcarbonyl amides.

As used herein, the term "prodrug" includes compounds which are hydrolyzable in vivo to yield an active compound, including for example, biohydrolyzable amides, biohydroiyzable esters and biohydrolyzable carbamates. The term "prodrug" also includes compounds in which the biohydrolyzable functionality is encompassed in the active compound.

As used herein, the term "affinity reagent" means a group attached to the active compound which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) Would be biotin either directly attached to the active compound or linked with a spacer of one to 50 atoms selected from the group consisting of: C, H, O, N, S, or P in any combination. An Example of an affinity reagent according to a) above would be fluorescein, either directly attached to the active compound or linked with a spacer of one to 50 atoms selected from the group consisting of: C, H, O, N, S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Although it is preferred to administer the CDK2 inhibitor agents in the practice of the present invention via topical application to susceptible skin areas for preventing/reducing the severity of alopecia incident to chemotherapy and/or radiation therapy, and via mouthwash formulation or lozenge for preventing/reducing the severity of mucositis incident to chemotherapy and/or radiation therapy, the CDK2 inhibitor agents in the practice of the invention can be otherwise administered in oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to combat the alopecia and/or mucositis condition.

Oral dosages in the practice of the present invention, when used for the indicated effects, will range between about 0.01 to about 100 mg/kg of body weight per day, and particularly about 0.1 to 10 mg/kg of body weight per day. Oral dosage units will generally be administered in the range of from 0.1 to about 250 mg and more preferably from about 25 to about 250 mg. The daily dosage or a 70 kg mammal will generally be in the range of about 70 mg to 7 grams of a DK2 inhibitor compound.

The dosage to be administered is based on the usual conditions such as the physical condition of the patient, age, body weight, past medical history, route of administrations, severity of the conditions and the like. In some cases, a relatively lower dose is sufficient and, in some cases, a relatively higher dose or increased number of doses may be necessary. Topical application may be once or more than once per day depending on.the course of chemotherapy and/or radiation therapy treatment. Advantageously, compounds of the present invention may be administered in a single daily dose, or the total daily dosage may be administered in divided doses of two, three or four times daily.

The compounds for use according to the present invention can be prepared in a range of concentrations for topical use of about 0.1 to about 5 mg/ml of suitable solvent. A preferred volume for application to the scalp is about 2 to 20 ml, resulting in an effective dosage delivered to the patient of about 0.2 to about 100 mg.

For treatment of chemotherapy-induced alopecia, administration 1 to 2 times prior to chemotherapy administration is preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using, those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by committing the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatinr, natural sugars such as glucose or beta-lactose, corn sweeteners, natural and synthetic gums such as acacia, tragacanth, or sodium alginate, carboxymethylcellulose, polyethylene glycol, waxes and the like. Lubricants used in these dosage forms include sodium oleate, sodium stearate, magnesium stearate, sodium, benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quate nary salt and/or an absorption agent such as bentonite, kaolin or dicalcium phosphate. The powder mixture can be granulated by wetting with a binder such as symp, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The coby pounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyes tuffs can be added to these coatings to distinguish different unit dosages.

Oral fluids such as solution syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds for use according to the present invention can also be administered in the form of liposome delivery, systems, such as small unilamellar vesicles, large unilamellar vesicles and multilamellar vesicles. Liposomes can be formed from a variety of phospholipids, such as cholesterol, stearylamine or phosphatidylcholines.

Compounds for use according to the present invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inihalation the compounds for use according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The inhibitory activity of various illustrative compounds may be determined against CDK2 kinase by the assay technique described below; the inhibitory activity may be determined as well against other kinases for comparison purposes (such as, for example, VEGFR2, Tie-2, and c-fms).

CDK1 and CDK2

Cyclin dependent protein kinase assays utilized the peptides Biotin-aminohexyl-AAKAKKTPKKAKK and Biotinaminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 nM), [γ-$^{32}$P]ATP (1–20 nM), and 10–20 mM Mg$^{2+}$ for periods of time generally within the range 10–120 min. Reactions were terminated with 0.2–2 volumes of either 20% acetic acid or 50–100 mM EDTA buffered to pH 7 (substrate consumption <20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following, either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM= $V_{max}*(1-([I]/(K+[I])))+nsb$, or pIC50s were determined by a fit to the equation CPM=nsb+$(V_{max}-nsb)/(1+(x/10^{x-pIC50}))$, where nsb are the background counts.

The results shown in Table 1 below illustrate the inhibitory activity of the illustrative compounds of formulae (A1), (A2) and (A3), as hereinbefore defined, against CDK2 and: CDK1.

TABLE 1

| Compound | CDK2 | CDK1 |
|---|---|---|
| A1 | ++++ | ++++ |
| A2 | +++ | ++ |
| A3 | ++++ | +++ |

Key (IC$_{50}$, nM)
1–10: ++++
11–50: +++
51–100: ++
>100: +

Protection from chemotherapy-induced alopecia may, for example, be determined in 7-day old Sprague-Dawley rat pups. Treatment is carried out by administering the compounds topically to the head of the animal in doses from 0.01 to 10 mg/kg 2 h before and 2 h after the administration of a single dose of 6 mg/kg etoposide intraperitoheally. Six days after dosing, animals are scored visually for hair loss using a grading scale from 1 (complete hair loss) to 4 (no apparent hair loss). In this assay, the prior treatment of the animal with a CDK2 inhibitor compound according to the present invention results in a marked reduction in the severity of alopecia compared to vehicle treated controls.

When the CDK2 inhibitor compounds are used to combat alopecia and/or mucositis in conjunction with the administration of chemotherapeutic agents or radiation therapy for cancer treatment, the CDK2 inhibitor compounds may be utilized to provide a secondary means of suppressing tumor growth either when administered simultaneously with the chemotherapeutic agents, or in an alternating regimen to suppress tumor growth between chemotherapeutic or radiation treatments.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invenion. It is intended, therefore, that the invention be limited only by the scope of the claims which follow and that such claims be interpreted as broadly as is reasonable. While the invention has been described herein with reference to specific features, aspects and embodiments, it will be appreciated that the scope of the invention is not thus limited, but rather extends to and encompasses other variations, modifications and other embodiments. Accordingly, the invention is to be correspondingly interpreted and constructed as including all such variations, modifications and other embodiments within its spirit and scope as hereinafter claimed.

BIBLIOGRAPHY

Throughout this specification various references have been cited, and the disclosures of all such references, as well as the following references, are incorporated herein by reference.

Cline, B. W., Prevention of chemotherapy-induced alopecia: A review of the literature, Cancer Nursing/June 1984, pp. 221–227.

Gray, N. S., et al., Exploiting Chemical Libraries, Structure, and Genomics in the Search for Kinase Inhibitors, Science, Vol. 284, Jul. 24, 1998, pp. 533–538.

Hussein, A. M., Chemotherapy-Induced Alopecia: New Developments, Southern Medical Journal, May 1993, Vol. 86, No. 5, pp. 489–496.

Hussein, A. M., et al., Protection from Chemotherapy-Induced Alopecia in a Rat Model, Science, Vol. 249, Sep. 28, 1990, pp. 1564–1566.

Lauer, A. C., et al., Transfollicular Drug Delivery, Pharmaceutical Research, Vol: 12, No. 2, 1995, pp. 179–186.

Li, L., et al., The feasibility of targeted selective gene therapy of the hair follicle, Nature Medicine, Voiurne 1, No. 7, July 1995, pp. 705–706.

Palumbo, Giuseppe A., et al., The Tyrphostin AG17 Induces Apoptosis and Inhibition of cdk2 Activity in a Lymphoma Cell Line That Overexpresses bcl-2, Cancer Research 57, 2434–2339, Jun. 15, 1997.

Roberts, James M., et al., U.S. Pat. No. 5,861,259 issued Jan. 19, 1999.

Sawaya, M. E., Alopecia—the search for novel agents continues, Exp. Opin. Ther. Patents (1997) 7(8): 859–872, Ashley Publications Ltd.

Sedlacek, Hans H:, et al., Flavopiridol (L86 82875; NSC 649890), a new kinase inhibitor for tumor therapy, international Journal of Oncology 9: 1143–1168, 1996.

Toledo, Leticia M., et al., Structures of staurosporine bound to CDK2 and cAPK—new tools for structure-based design of protein kinase inhibitors, Structure 1997, Vol. 5 No. 12, pp. 1551–1556.

The application of which this description and claim(s) forms part may be used as a basis for priority in respect of any subsequent application. The claims of such subsequent application may be directed to any feature or combination of features described herein. They may take the form of product, formulation, process or use claims and may include, by way of example and without limitation, one or more of the following claim(s):

What is claimed is:

1. A method of reducing the severity of mucositis and/or plantar palmar side-effects of chemotherapy and/or radiation therapy in a subject receiving such therapy, comprising administerung to said subject an effective amount of a cyclin-dependent kinase II inhibitor, wherein said dependent kinase II inhibitor is a compound of formula (A):

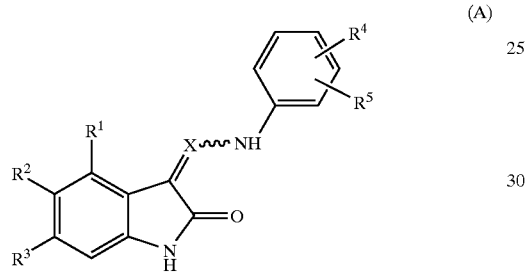

wherein:

X is N, CH, CCF$_3$, or C(C$_{1-12}$ aliphatic);

R$^1$ is selected from the group consisting of: hydrogen, C$_{1-12}$ aliphatic, thiol, hydroxy, hydroxy-C$_{1-12}$ aliphatic, aryl, aryl-C$_{1-12}$ aliphatic, R$^6$-aryl-C$_{1-12}$ aliphatic, Cyc, Cyc-C$_{1-6}$ aliphatic, Het, Het-C$_{1-12}$ aliphatic, C$_{1-12}$ alkoxy, aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halo, cyano, sulfonamide, or nitro;

R$^2$ is selected from the group consisting of: hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{1-12}$ alkoxycarbonyl, carboxyl C$_{1-12}$ aliphatic, aryl, R$^6$-aryl-oxycarbonyl, R$^6$-oxycarbonyl-aryl, Het, aminocarbonyl, C$_{1-12}$ aliphatic-aminocarbonyl, aryl-C$_{1-12}$ aliphatic-aminocarbonyl, R$^6$-aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halo, hydroxy, nitro, C$_{1-12}$ aliphatic-sulfonyl, aminosulfonyl, and C$_{1-12}$ aliphatic-aminosuifonyl;

wherein R$^1$ and R$^2$ are optionally joined to form a fused ring selected from the group as defined for Het below, and said fused ring is optionally substituted by C$_{1-12}$ aliphatic, halogen, nitro, cyano, C$_{1-12}$ alkoxy, amino, hydroxyl, carbo-C$_{1-12}$ alkoxy, or oxo;

R$^3$ is selected from the group consisting of: hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$ alkoxy, aryl, aryloxy, hydroxy-aryl, Het, hydroxy-Het, Het-oxy, or halo;

further wherein R$^2$ and R$^3$ are optionally joined to form a fused ring selected from the group as defined for Het below, and said fused ring is optionally substituted by C$_{1-6}$ aliphatic or C$_{1-6}$ aliphatic-carbonyl;

with the proviso that R$^1$, R$^2$ and R$^3$ cannot simultaneously be hydrogen;

R$^4$ is selected from the group consisting of: suifonic acid, C$_{1-12}$ aliphatic-sulfonyl, sulfonyl-C$_{1-12}$ aliphatic, C$_{1-6}$ aliphatic-amino, R$^7$-sulfonyl, R$^7$-sulfonyl-C$_{1-12}$ aliphatic, R$^7$-aminosulfonyl, R$^7$-sulfonyiamino-C$_{1-12}$ aliphatic, aminosulfonylamino, di-C$_{1-12}$ aliphatic amino, di-C$_{1-12}$ aliphatic aminocarbonyl, di-C$_{1-12}$ aliphatic aminosulfonyl, di-C$_{1-12}$ aliphatic amino, di-C$_{1-12}$ aliphatic aminocarbonyl, di-C$_{1-12}$ aliphatic aminosulfonyl-C$_{1-12}$ aliphatic, (R$^8$)$_{1-3}$-arylamino, (R$^8$)$_{1-3}$-arylsulfonyl, (R$^8$)$_{1-3}$-arylaminosulfonyl, (R$^8$)$_{1-3}$-arylsulfonylamino, Het-amino, Het-sulfonyl, Het-aminosulfonyl, aminoiminoamino, or aminoiminoaminosulfonyl, where R$^7$, R$^8$, aryl and Het are as defined below;

R$^5$ is hydrogen;

and further wherein R$^4$ and R$^5$ are optionally joined to form a fused ring, said ring being selected from the group as defined for Het below, or any of said fused rings optionally substituted by C$_{1-12}$aliphatic, oxo or dioxo;

R$^6$ is selected from the group consisting of C$_{1-12}$aliphatic, hydroxy, C$_{1-12}$alkoxy, or halo;

R$^7$ is selected from the group consisting of: hydrogen, C$_{1-12}$ aliphatic, C$_{1-12}$ alkoxy, hydroxy-C$_{1-12}$ alkoxy, hydroxy-C$_{1-12}$ aliphatic, carboxylic acid, C$_{1-12}$ aliphatic-carbonyl, Het, Het-C$_{1-12}$ aliphatic, Het-C$_{1-12}$ alkoxy, di-Het-C$_{1-12}$ alkoxy aryl, aryl-C$_{1-12}$ aliphatic, aryl-C$_{1-12}$ alkoxy, aryl-carbonyl, C$_{1-18}$ alkoxyalkoxyalkoxyalkoxyaliphatic, or hydroxyl;

R$^8$ is selected from the group consisting of: hydrogen, nitro, cyano, C$_{1-12}$ alkoxy, halo, carbo-C$_{1-12}$ alkoxy and halo-C$_{1-12}$ aliphatic;

aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiadzole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole;

and the pharmaceutically acceptable salts, solvates, prodrugs thereof in either crystalline or amorphous form.

2. The method of claim 1, wherein said epithelial cytoxicity side effects comprise plantar-paimar syndrome.

3. The method of claim 1, wherein said epitnelial cytoxicity side effects comprise mucositis.

4. The method of claim 1, wherein said cyclin-dependent kinase II inhibitor is administered in a topically applied formulation to corporeal loci susceptible to epithelial cytoxicity induced by chemotherapy and/or radiation therapy.

5. The method of claim 1, wherein said cyclin-dependent kinase II inhibitor is topically administered to the hands and/or feet to reduce the severity of chemotherapy-induced plantar-palmar syndrome.

6. The method of claim 1, wherein said cyclin-dependent kinase II inhibitor is topically administered to oral cavity mucosa to reduce the severity of chemotherapy-induced mucositis.

7. The method of claim 1, wherein said cyclin-dependent kinase II inhibitor is topically administered to oral cavity mucosa to reduce the severity of radiation therapy-induced mucositis.

8. The method of claim 1 wherein said cyclin-dependent kinase II inhibitor is characterised by at least one of the following IC50 characteristics:

(a) an IC50 value of less than 2.5 nanoMolar against CDK2; and
(b) an IC50 value of.less than 1.5 microMolar in a G1 checkpoint assay.

9. The method of claim 1, wherein said administration of the cyclin-dependent kinase II inhibitor comprises non-systemic administration.

10. The method of claim 1, wherein said cyclin-dependent kinase II inhibitor is administered contemporaneously with a radiation therapy treatment having an epithelial cytoxicity side effect.

11. The method of claim 1, wherein said cyclin-dependent kinase II inhibitor is administered contemporaneously with a chemotherapeutic treatment having an epithelial cytoxicity side effect.

12. The methodof claim 1, wherein said cyclin-dependent kinase II inhibitor is administered 1–4 times in a chemotherapeutic cycle.

* * * * *